(12) United States Patent
de Both et al.

(10) Patent No.: US 8,674,175 B2
(45) Date of Patent: Mar. 18, 2014

(54) FARNESENE SYNTHASE

(75) Inventors: Michiel Theodoor Jan de Both, Wageningen (NL); Robert Cornelis Schuurink, Amsterdam (NL); Kai Ament, Amsterdam (NL); Michael Albertus Haring, Haarlem (NL)

(73) Assignee: Keygene N.V., Wageningen (NL)

( * ) Notice: Subject to any disclaimer, the term of this patent is extended or adjusted under 35 U.S.C. 154(b) by 188 days.

(21) Appl. No.: 13/132,702

(22) PCT Filed: Dec. 2, 2009

(86) PCT No.: PCT/NL2009/000244
§ 371 (c)(1),
(2), (4) Date: Aug. 30, 2011

(87) PCT Pub. No.: WO2010/064897
PCT Pub. Date: Jun. 10, 2010

(65) Prior Publication Data
US 2011/0307972 A1    Dec. 15, 2011

Related U.S. Application Data

(60) Provisional application No. 61/120,179, filed on Dec. 5, 2009.

(51) Int. Cl.
*C07K 14/00* (2006.01)
*C12N 15/00* (2006.01)
*C12N 15/05* (2006.01)
*C12N 15/10* (2006.01)
*C12N 5/14* (2006.01)

(52) U.S. Cl.
USPC ....... 800/278; 435/91.1; 435/320.1; 435/419; 530/350; 800/298

(58) Field of Classification Search
None
See application file for complete search history.

(56) References Cited

PUBLICATIONS

Bleeker et al, 2011, Plant Mol. Bio., 77:323-336.*
Deligeorgopoulou et al, 2003, Biochemistry, 42:7741-7747.*
Jimenez et al, 2004, PubMed Accession No. Q2TJK5.*
Jimenez et al, 2004, PubMed Accession No. AY860847.*

* cited by examiner

*Primary Examiner* — Ashwin Mehta
*Assistant Examiner* — Jason Deveau Rosen
(74) *Attorney, Agent, or Firm* — Foley & Lardner LLP; Richard C. Peet (57) ABSTRACT

A new farnesene synthase was isolated from tomato. The farnesene synthase shows surprising properties with regard to the end products formed and its gene has, on a nucleotide level, low sequence identity with known farnesene synthase genes from other sources. The invention relates to isolated polynucleotides, polypeptides encoded by said polynucleotides, genetic constructs, vectors, hosts, in particular plants, harboring such polynucleotides, polypeptides and genetic constructs, and seed derived from such plants.

11 Claims, 6 Drawing Sheets

Total Sol.

FARNESENE SYNTHASE

SUMMARY

A new farnesene synthase was isolated from tomato. The farnesene synthase shows surprising properties with regard to the end products formed and its gene has, on a nucleotide level, low sequence identity with known farnesene synthase genes from other sources. The invention relates to isolated polynucleotides, polypeptides encoded by said polynucleotides, genetic constructs, vectors, hosts, in particular plants, harbouring such polynucleotides, polypeptides and genetic constructs, and seed derived from such plants.

1. Technical Field

The present invention relates to a farnesene synthase enzyme, in particular to an alpha-farnesene synthase and/or a beta-farnesene synthase. It also relates to polynucleotide sequences encoding such enzyme. The invention also relates to nucleic acid (or genetic) constructs, vectors and host cells incorporating the polynucleotide sequences. It further relates to the production of alpha-farnesene and/or beta-farnesene, and the use thereof.

2. Background Art

The term farnesene refers to a set of six closely related chemical compounds which all are sesquiterpenes. Alpha-Farnesene and beta-farnesene are isomers, differing by the location of one double bond. Alpha-Farnesene is 3,7,11-trimethyl-1,3,6,10-dodecatetraene and beta-farnesene is 7,11-dimethyl-3-methylene-1,6,10-dodecatriene. Alpha-farnesene can exist as four stereoisomers that differ in the geometry of two of its three internal double bonds (the stereoisomers of the third internal double bond are identical). Beta-farnesene exists as two stereoisomers in the geometry of its central double bond. There is only limited understanding with respect to the differences between the various isomers of both alpha-farnesene and beta-farnesene, in relation to the specific function of these isomers.

Alpha-farnesene is either constitutively present or induced in a wide range of species (Gapper et al., Postharvest Biology and Technology 42: (2006) 225-233). Alpha-farnesene is believed to be synthesised from farnesyl diphosphate (FDP) in a reaction that proceeds through a carbocation intermediate, and is reported to be catalysed by the enzyme alpha-farnesene synthase (Rupasinghe, et al., J. Am. Soc. Hortic. Sci. 123,882-886 (1998)).

Beta-farnesene occurs in a wide range of both plant and animal taxa. Various papers have been published on the occurrence of this natural product and its deployment as an important courier in chemical communication. Beta-farnesene is found in the essential oil of many species of both gymnosperms and angiosperms, including *Chamomilla recutita, Vitis vinifera, Zea mays*, and *Piper nigrum*. (E)-beta-farnesene synthase is being induced by Egyptian cotton leafworm (*Spodoptera littoralis*) herbivory in maize sheath and leaf tissue, but not in root tissues (Schnee et al., Plant Physiol., 2002, 130: 2049-2060). Beta-farnesene is believed to be synthesized from FDP, in a reaction involving divalent metal ion-assisted ionization of the diphosphate ester and deprotonation from the C-3 methyl of the resulting carbocation, as disclosed in WO1999/18118.

Among its functions, alpha-farnesene is described as an insect attractant and acts as a sex pheromone in mice and insects. It acts as an alarm pheromone in *Prorhinotermes canalifrons* (Sobotnik et al. (2008) J. Chem. Ecol. 34(4):478-86). Other uses for alpha-farnesene and its derivatives are as potent cancer prevention agents, and in plastic film synthesis (US20060137032. Hernández-ceruelos et al. (Toxicol. Lett. 135: 103-110, 2005) report on the antimutagenic effects of β-farnesene, the major component of essential chamonile oil, on mouse bone marrow cells after mutagenic treatments.

Beta-farnesene has been described as a major component of pollen odour in *Lupinus* and stimulates pollination behaviour in bumblebees (Dobson et al. (1996) Am. J. Bot. 83, 877-885). More importantly, the use of beta-farnesene by aphid species as an alarm pheromone has been described, e.g. for *Aphis gossypii* (cotton aphid) (Jianwei et al., 2006, J. Econ. Entomol. 99 (5): 1636-1640; Kislow and Edwards, 1972, Nature 235: 108-109; Pickett and Griffiths, 1980, J. Chem. Ecol. 6: 349-360 and for *Myzus persicae* (green peach aphid) (Edwards, L. J., 1973, Nature 241: 126-127) Aphids exposed to beta-farnesene become agitated and disperse from their host plant (Wohlers (1981) Z Angew. Entomol. 92, 329-336). Beta-farnesene is acutely toxic to aphids at a dose of 100 ng/aphid (van Oosten et al. (1990) Acta Phytopathol. Entomol. Hung. 25, 331-342). Also of interest is the notion that beta-farnesene vapour is toxic to whiteflies (Klijnstra et al. (1992) Meded Fac. Landbouwwet. 57, 485-491). Unfortunately, efforts to control aphid behaviour by topical application of beta-farnesene to crops have met with little success, due to volatility and rapid oxidative inactivation in air (Dawson et al. (1988) Pest. Sci. 22, 17-30).

Schnee et al (Plant Physiology Vol. 130, pp 2049 (2002) describes a terpene synthase catalyzing the formation of (E)-beta-farnesene. WO2004/035791 discloses an alpha-farnesene synthase from *Malus domestica*. WO99/18118 discloses a (E)-beta farnesene synthase from *Mentha piperita*.

SUMMARY OF THE INVENTION

In a first aspect there is provided a polynucleotide according to SEQ ID NO:1., and homologues thereof. The nucleotide can encode a polypeptide with farnesene synthase activity, in particular alpha-farnesene synthase activity and/or beta-farnesene synthase activity.

In a further aspect the invention provides for a polypeptide according to SEQ. ID. NO:2., and homologues thereof. The polypeptide can have farnesene synthase activity, in particular alpha-farnesene synthase activity and/or beta-farnesene synthase activity.

In yet a further aspect the invention provides for a genetic construct, a vector comprising such genetic construct, and a host cell comprising such genetic construct, wherein the genetic construct comprises a polynucleotide according to the invention.

In yet a further aspect the invention provides for a transgenic plant or plant cell comprising such genetic construct, and seed derived from such plants or plant cells.

In yet a further aspect there is provided for a method for preparing alpha-farnesene and/or beta-farnesene comprising the use of a polynucleotide according to the invention.

In yet an even further aspect, there is provided for a method for modulating the alpha-farnesene and/or beta-farnesene production of a plant, comprising regulation of the expression level of polypeptides encoded by the polynucleotides according to the invention.

The foregoing aspects and other advantages of this invention will become more readily appreciated as the same becomes better understood by reference to the following detailed description and examples, when taken in conjunction with the accompanying drawings, the description of which is given in the description and example.

Definitions

In the following description and examples several terms are used. In order to provide a clear and consistent understanding of the specification and claims, including the scope to be given to such terms, the following definitions are provided. Unless otherwise defined herein, all technical and scientific terms used have the same meaning as commonly understood by one of ordinary skill in the art to which this invention belongs. The disclosures of all publications, patent applications, patents and other references are incorporated herein in their entirety by reference.

"Farnesene synthase" refers to an enzyme that is capable of converting farnesyl diphosphate to alpha-farnesene and/or beta-farnesene.

"Farnesene synthase activity" refers to the ability of the farnesene synthase of the present invention to catalyze the formation of alpha-farnesene, beta-farnesene or both from farnesyl diphosphate. Activity is measured in an enzyme activity assay, such as the assay described in the example. Amino acid sequence variants of the farnesene synthases of the present invention may have desirable altered biological activity including, for example, altered reaction kinetics, substrate utilization, product distribution or other characteristics such as stereochemistry.

"Genetic construct" refers to a polynucleotide molecule, usually double-stranded DNA, which may have inserted into it another polynucleotide molecule (the insert polynucleotide molecule) such as, but not limited to, a cDNA molecule. A genetic construct may contain the necessary elements that permit transcribing the insert polynucleotide molecule, and, optionally, translating the transcript into a polypeptide. The insert polynucleotide molecule may be derived from the host cell, or may be derived from a different cell or organism and/or may be a recombinant polynucleotide. Once inside the host cell the genetic construct may become integrated in the host chromosomal DNA. The genetic construct may be linked to a vector.

The term "gene" means a DNA sequence comprising a region (transcribed region), which is transcribed into an RNA molecule (e.g. an mRNA) in a cell, operably linked to suitable regulatory regions (e.g. a promoter). A gene may thus comprise several operably linked sequences, such as a promoter, a 5' leader sequence comprising e.g. sequences involved in translation initiation, a (protein) coding region (cDNA or genomic DNA) and a 3'non-translated sequence comprising e.g. transcription termination sites.

"Host cell" refers to a prokaryotic or a eukaryotic cell. Typical prokaryotic host cells include various strains of *E. coli*. Typical eukaryotic host cells are plant cells, yeast cells, insect cells or animal cells.

"Percent sequence identity" means the percentage of amino acids or nucleotides that occupy the same relative position when two amino acid sequences, or two nucleic acid sequences, are aligned side by side. The length of sequences to be compared for nucleic acids is generally at least 120 nucleotides, preferably 200 nucleotides and more preferably 300 nucleotides and the length of sequences to be compared for polypeptides is generally at least 40 amino acid residues, preferably 65 amino acid residues and more preferably 100 amino acid residues. Preferably "percent sequence identity" is determined by using Clustal W alignments.vClustalW alignments were carried out using the software program "CLC Free Workbench 3" of the company CLC Bio, Cambridge, Mass., USA. This program is freely available from CLC Bio's website. The parameters used for both nucleotide and amino acid alignments are a gap open penalty of 10 and a gap extension penalty of 1. Gap-ends were regarded as all other gaps.

"Polynucleotide(s)" as used herein means a single or double-stranded polymer of deoxyribonucleotide or ribonucleotide bases and includes DNA and corresponding RNA molecules, both sense and anti-sense orientations, and comprehends cDNA, genomic DNA and recombinant DNA, as well as wholly or partially synthesized polynucleotides. A polynucleotide may consist of an entire gene, or any portion thereof. Operable anti-sense polynucleotides may comprise a fragment of the corresponding polynucleotide, and the definition of "polynucleotide" therefore includes all such operable anti-sense fragments.

"Isolated polynucleotide" is a nucleotide molecule that is identified and separated from at least one contaminant polynucleotide with which it is ordinarily associated.

"Polypeptide(s)" as used herein includes peptides, polypeptides and proteins.

"Isolated polypeptide" is a polypeptide that has been identified and separated or recovered to be largely free of components of its natural environment. It includes polypeptides in situ within recombinant cells. However, generally isolated polypeptides are prepared by at least one purification step.

The term "genetic marker" or "polymorphic marker" or "molecular marker" refers to a region on the genomic DNA which can be used to "mark" a particular location on the chromosome. If a genetic marker is tightly linked to a gene or is 'in' a gene it "marks" the DNA on which the gene is found and can therefore be used in a (molecular) marker assay (see below) to select for or against the presence of the gene, e.g. in marker assisted breeding/selection (MAS) methods. Examples of genetic markers are AFLP (amplified fragment length polymorphism), microsatellite, RFLP (restriction fragment length polymorphism), STS (sequence tagged site), SNP (Single Nucleotide Polymorphism), SFP (Single Feature Polymorphism; see Borevitz et al. 2003, Genome Research 13: 513-523), SCAR (sequence characterized amplified region), CAPS markers (cleaved amplified polymorphic sequence) and the like. The further away the marker is from the gene, the more likely it is that recombination (crossing over) takes place between the marker and the gene, whereby the linkage (and co-segregation of marker and gene) is lost. The distance between genetic loci is measured in terms of recombination frequencies and is given in cM (centiMorgans; 1 cM is a meiotic recombination frequency between two markers of 1%). As genome sizes vary greatly between species, and as the distribution of recombination events is not random over the genome, the actual physical distance represented by 1 cM (i.e. the kilobases, kb, between two markers) also varies greatly between and within species. It is understood that, when referring to markers or "linked" markers herein, this also encompasses markers "in" the gene itself.

A "molecular marker assay" (or test) refers to a (DNA based) assay that indicates (directly or indirectly) the presence or absence of a polynucleotide according to the invention in a plant or plant part.

DETAILED DESCRIPTION

It is an object of the invention to provide for new polynucleotide sequences encoding farnesene synthases, enzyme(s) encoded by such nucleotides, methods for in vitro synthesis of alpha-farnesene and/or beta-farnesene, and/or genetically modifying plants to alter their levels of alpha-farnesene and/or beta-farnesene activity, and provide the public with useful choice in available enzymes.

It has surprisingly been found that the above problem can be solved by providing an isolated polynucleotide according to SEQ ID No: 1, or a polynucleotide that has at least 50%, preferably at least 60%, more preferably at least 70%, even more preferably at least 90%, most preferably at least 95% sequence identity to the nucleotide sequence of SEQ ID NO: 1. Preferably, said polynucleotide encodes a farnesene synthase, i.e. for an enzyme that can synthesize a alpha-farnesene and/or a beta-farnesene from an suitable substrate. Therefore, in another embodiment there is provided a polynucleotide according to the invention, wherein said polynucleotide encodes a polypeptide with farnesene synthase activity.

The nucleotide of SEQ ID NO: 1, and according to the invention, is the coding sequence of a farnesene synthase gene encoding a farnesene synthase obtained from a tomato plant, *Solanum lycopersicon* cultivar Money Maker, as described in detail in the methods. As will be explained in further detail below, the farnesene synthase according to the invention has surprising characteristics in comparison to farnesene synthases known in the art, not only with respect to differences in sequence identity of the polynucleotides, but, importantly, with respect to the activity of the farnesene synthase encoded by such polynucleotide.

As will be understood by the skilled person, also provided are such polynucleotides that have at least 50%, preferably at least 60%, more preferably at least 70%, even more preferably at least 90%, most preferably at least 95% sequence identity to the nucleotide sequence of SEQ ID NO: 1.

Within the context of the current invention, sequence identity can be and was determined by using ClustalW alignment. ClustalW alignments were carried out using the software program "CLC Free Workbench 3" of the company CLC Bio, Cambridge, Mass., USA. This program is freely available from the website http://www.clcbio.com. The parameters used for both nucleotide and amino acid alignments are a gap open penalty of 10 and a gap extension penalty of 1. Gap-ends were regarded as all other gaps.

Using said ClustalW alignment it was calculated that the polynucleotide according to SEQ. ID. NO:1 shows (only) 36% identity with a known E-beta-farnesene synthase isolated from *Zea mays* (Schee et al. 2002), 46% identity with a known alpha-farnesene synthase isolated from *Malus domesticus* (WO2004/035791), and 48% identity with a known E-beta-farnesene synthase from *Mentha×piperita* (WO99/18118).

In another embodiment, the current invention also provides for polynucleotides that differ from the polynucleotide according to SEQ. ID. NO:1 with respect to 20, 15, 10, 9, 8, 7, 6, 5, 4, 3, 2, or 1 nucleotide(s), by insertion, deletion or substitution in the polynucleotide sequence according to SEQ. ID. NO:1. Such insertions, deletions or substitutions can be with respect to adjacent nucleotides, but can also be present on different, for example 2,3,4, or 5, positions within the polynucleotide according to SEQ. ID. NO:1. For example, a nucleotide at a first position can be deleted, two nucleotides at a second position can be substituted, whereas at a third position within the polynucleotide according to SEQ.ID.NO:1 one or more nucleotides are inserted.

The (isolated) polynucleotide according to the invention can be in the form of a cDNA, or the corresponding RNA, a synthetic polynucleotide, but also includes a polynucleotide comprising both introns and exons. As will be understood by the skilled person, the polynucleotide according to the invention can further comprise, in addition to a region encoding for a farnesene synthase according to the invention, regulatory sequences, including, preferably a promoter region, for example a promoter region of the farnesene synthase according to the invention.

Also provided are fragments of a polynucleotide according to the invention, as long as such fragment of the polynucleotide according to the invention encodes a polypeptide having farnesene activity. Farnesene activity can be determined by various methods known in the art, but is preferably determined as described in detail in the enclosed examples.

As discussed above, it has been found that the polynucleotide according to the invention, for example the polynucleotide according to SEQ.ID.NO:1, encodes a polypeptide with farnesene activity. In particular, it has been found that the polypeptide according to the invention encodes a polypeptide capable of forming alpha-farnesene and/or beta-farnesene. The polynucleotide according to the invention, can, in this embodiment, thus be used for forming alpha-farnesene and/or beta-farnesene.

In addition, results showed the presence of (+)-valencene, suggesting that the polypeptides according to the invention can be used for forming (+)-valencene as well. Therefore, in the description herein, where reference is made to the polypeptide according to the invention, in addition to alpha-farnesene synthase activity and/or beta-farnesene synthase activity, the polypeptide according to the invention might also show (+)-valencene synthase activity, i.e form (+)-valencene.

Alpha-farnesene can exist in the form of four different stereoisomers: (Z,E)-alpha-farnesene, (Z,Z)-alpha-farnesene, (E,Z)-alpha-farnesene and (E,E)-alpha-farnesene. Beta-farnesene can exist in two different stereoisomers: (E)-beta-farnesene and (Z)-beta-farnesene.

In a further embodiment there is provided a polynucleotide according to the invention wherein the polynucleotide encodes a polypeptide with alpha-farnesene synthase activity and beta-farnesene synthase activity.

It was surprisingly found that the polynucleotide(s) according to the invention can encode polynucleotide(s) according to the invention that are capable of both synthesizing alpha-farnesene and beta-farnesene, as shown in the examples. In contrast, other farnesene synthases known to the applicant, for example, those disclosed in WO2004/035791 and WO99/18118, have only been described as forming either alpha-farnesenes or beta-farnesenes. For example, and preferably, the polynucleotide(s) according to the invention can encode polynucleotide(s) according to the invention that are capable of synthesizing (E)-beta-farnesene, (Z,E)-alpha-farnesene, (E,E)-alpha-farnesene and (Z,Z)-alpha-farnesene.

It was found that, for example, the polypeptide encoded by a polynucleotide according to SEQ.ID.NO:1, has activity towards both the synthesis of alpha-farnesene and beta-farnesene (in particular (E)-beta-farnesene, (Z,E)-alpha-farnesene, (E,E)-alpha-farnesene and (Z,Z)-alpha-farnesene). It was now for the first time found that a polynucleotide according to the invention, for example isolated from tomato plant (*Solanum lycopersicon* cultivar Money Maker), encodes a polypeptide having the property of synthesizing both different stereoisomers of alpha-farnesene and beta-farnesene. Indeed, the synthesis of both alpha-farnesene and beta-farnesene in such tomato plant, e.g. *Solanum lycopersicon* cultivar Money Maker, has not been described before and is surprising.

This now allows for the first time to provide for a polynucleotide according to the invention that can be used for forming alpha-farnesene, beta-farnesene, or both. In addition, this allows now for the first time to use such polynucleotide and encoded polypeptide to further elucidate the relationship between the polynucleotide and encoded polypeptide and its activity with respect to the synthesis of the different farnesenes, both in vivo and in vitro. For example, it can be understood that mutants can be obtained having, for example, (increased) beta-farnesene synthase activity, and not (or reduced) alpha-farnesene synthase activity. Amino acid sequence variants of the farnesene synthases of the present invention may also have desirable altered biological activity including, for example, altered reaction kinetics, substrate utilization, product distribution or other characteristics such as stereochemistry.

In addition, with the polynucleotides and polypeptides according to the invention, it has now become possible to synthesize specific mixtures or blends of alpha-farnesene and/or beta-farnesene, both in vivo and in vitro, while using only one polynucleotide or polypeptide. For example, the polynucleotide according to the invention can be introduced in a plant or bacteria, or a polypeptide according to the invention can be used in an in vitro system for synthesising alpha-farnesene and/or beta-farnesene.

With the polynucleotide according to the invention one has an effective means of controlling the synthesis of different farnesenes, as will be explained in more detail below, since the gene can be used for transforming, for example, susceptible plant genotypes thereby producing genetically transformed plants having an altered synthesis of different types of farnesenes.

In a preferred embodiment of the polynucleotide according to the invention, there is provided for an isolated polynucleotide encoding a polypeptide according to SEQ ID NO:2, or a polypeptide that has at least 50%, preferably at least 60%, more preferably at least 70%, even more preferably at least 90%, most preferably at least 95% sequence identity with the amino acid sequence according to SEQ ID NO:2.

It has been found that in particular a polynucleotide encoding a polypeptide according to SEQ ID NO:2, or a polypeptide that has at least 50%, preferably at least 60%, more preferably at least 70%, even more preferably at least 90%, most preferably at least 95% sequence identity with the amino acid sequence according to SEQ ID NO:2. can advantageously be used within the context of the current invention.

In another embodiment there is provided a fragment of a polynucleotide according to the invention wherein the fragment encodes a polypeptide with alpha-farnesene synthase activity and/or beta-farnesene activity, preferably wherein the fragment encodes a polypeptide with alpha-farnesene activity and/or beta-farnesene synthase activity.

Without leaving the scope of the current invention, it will be understood that in addition to the polynucleotides described above, several modifications to the polynucleotides according to the invention are possible, without such modifications substantially deteriorating the activity of the polypeptide encoded by such modified polynucleotide. For example, as already explained above, the polynucleotide according to the invention can comprise such modifications like deletions, substitutions and insertions without substantially interfering with the activity of the encoded polypeptide. Therefore also fragments of the polynucleotides according to the invention that encode polypeptides which show alpha-farnesene activity and/or beta-farnesene synthase activity (preferably both), are provided in the current invention. Such fragment is not constrained to a particular size or part of the polynucleotide according to the invention as long as it has alpha-farnesene activity and/or beta-farnesene synthase activity (preferably both). The skilled person can easily establish whether such fragment of the polynucleotide according to the invention has the required activity by applying the methods given in the examples, or by any other suitable method known in the art.

In another aspect the invention relates to the polypeptides encoded by the polynucleotides according to the invention. In particular there is provided for a polypeptide according to SEQ ID NO: 2, or a polypeptide that has at least 50%, preferably at least 60%, more preferably at least 70%, even more preferably at least 90%, most preferably at least 95% sequence identity to the amino acid sequence according to SEQ ID NO:2., as can be determined by ClustalW alignment as described above.

In another embodiment, the current invention also provides for such polypeptides that differ from the polypeptide according to SEQ. ID. NO:2 with respect to 20, 15, 10, 9, 8, 7, 6, 5, 4, 3, 2, or 1 amino acid(s), by insertion, deletion or substitution in the polypeptide sequence according to SEQ. ID. NO:2. Such insertions, deletions or substitutions can be with respect to adjacent amino acids, but can also be present on different, for example 2,3,4, or 5, positions within the polypeptide according to SEQ. ID. NO:2. For example, an amino acid at a first position can be deleted, one amino acid at a second position can be substituted, whereas at a third position within the polypeptide according to the SEQ.ID.NO:2 one or more nucleotides are inserted.

In a preferred embodiment, such polypeptides according to the invention have farnesene synthase activity, preferably alpha-farnesene activity and/or beta-farnesene synthase activity, more preferably alpha-farnesene activity and beta-farnesene synthase activity. However, this is not to be construed to exclude such polypeptides according to the invention that are devoid of both activities (e.g. mutants).

In another embodiment, there is provided an isolated alpha-farnesene and beta-farnesene synthase polypeptide. Such polypeptide according to the invention is active towards both the synthesis of alpha-farnesene and beta-farnesene, for example as can be determined as described in the examples. As discussed above, it is now for the first time that such polypeptide has been isolated (from a tomato plant (Solanum lycopersicon cultivar Money Maker)), and which polypeptide can advantageously be employed as described herein.

In another embodiment there is provided a fragment of a polypeptide according to the invention, wherein the fragment has alpha-farnesene synthase activity and/or beta-farnesene activity, preferably alpha-farnesene and beta-farnesene synthase activity.

Without leaving the scope of the current invention, it will be understood that in addition to the polypeptides described above, several modifications to the polypeptides are possible, without such modifications substantially deteriorating the activity of the polypeptide. For example, as already explained above, the polypeptide according to the invention can comprise such modifications like deletions, substitutions and insertions of amino acids without substantially interfering with the activity of the polypeptide. Therefore also fragments of the polypeptides according to the invention and which have alpha-farnesene activity and/or (preferably and) beta-farnesene synthase activity, are provided by the current invention. Such fragment is not constrained to a particular size of part of the polypeptide according to the invention as long as it has alpha-farnesene activity and/or beta-farnesene synthase activity. The skilled person can easily establish whether such fragment according to the invention has the required activity by applying the methods given in the examples, or by any other suitable method known in the art.

The polypeptide according to the invention, or a fragment thereof can, in addition to its farnesene synthase activity, for example be used for raising antibodies against it and which antibodies can be used for the detection of a polypeptide according to the invention, for example in plants.

In another aspect of the invention, the polynucleotides according to the invention can be used for the design of oligonucleotides which are complementary to one strand of the DNA sequence of a polynucleotide according to the invention, preferably a polynucleotide sequence according to SEQ.ID.NO:1, or part thereof, and which can be used as hybridization probes, being labelled to allow detection, for the screening of genomic DNA or cDNA libraries for homologous genes. Homologous sequences which can hybridize to the probe under high stringent hybridization conditions, and which encode a gene product that is involved in farnesene synthase, preferably having alpha-farnesene synthase and/or beta-farnesene synthase activity are comprised within the scope of the present invention.

In general, high stringent conditions refer to the (Southern) hybridization conditions which allow a nucleic acid sequence of at least 50 nucleotides and preferably about 200 or more nucleotides to hybridize to a particular sequence at about 65° C. in a solution comprising about 1 M salt, preferably 6×SSC or any other solution having a comparable ionic strength, and washing at 65 C in a solution comprising about 0.1 M salt, or less, preferably 0.2×SSC or any other solution having a comparable ionic strength (Sambrook, Maniatis, Fritsch, Molecular Cloning, A Laboratory Manual, CSHL Press, USA, 1987)). These conditions allow the detection of sequences having about 90% or more sequence identity.

In another aspect of the invention oligonucleotides are designed based on the polynucleotide according to the invention, such that they can be used as hybridization probes in Southern analysis. These probes can be used as molecular markers to distinguish plant genotypes having a farnesene synthase according to the invention and plant genotypes lacking such farnesene synthase. Such a probe can be used as an additional tool in selection.

For example, they can be used in a method of detecting the presence or absence of a nucleotide sequence according to the invention, encoding a polypeptide according to the invention in a plant tissue or nucleic acid sample thereof comprising:
  a. Obtaining a plant tissue sample or a nucleic acid sample,
  b. Analyzing the sample using a molecular marker assay for the presence or absence of one or more markers linked to the polypeptide according to the invention, wherein the marker assay detects a sequence according to SEQ ID No: 1, or a sequence that has at least 50%, preferably at least 60%, more preferably at least 70%, even more preferably at least 90%, most preferably at least 95% sequence identity to the nucleotide sequence of SEQ ID NO: 1.

In a preferred embodiment of the invention, oligonucleotides are designed based on the polynucleotide according to the invention, such that they can be used as primers in an amplification reaction, such as polymerase chain reaction (PCR), whereby the formation of an amplification product indicates the presence of a farnesene synthase, preferably a farnesene synthase according to the invention, in a certain plant genotype.

In a preferred embodiment, said primers are used in selective restriction fragment amplification to identify AFLP markers, which are closely linked to a farnesene synthase gene according to the invention. Indeed, an exceptionally useful technique is the AFLP technique, as described by Vos, P. et al., in Nucleic Acids Research, 1995, Vol. 23, No. 21: 4407-4414.

Molecular markers can now in fact be derived from the polynucleotides according to the invention. Indeed the provided nucleotide sequences can be applied as genetic markers for use in molecular breeding methods and germplasm screening and/or characterization. Such markers can be used in marker assisted selection of plants having or not having a polynucleotide or polypeptide according to the invention.

Therefor there is provided for the use of at least 15 consecutive nucleotides of SEQ ID NO: 1, or a sequence comprising at least 90% nucleotide identity thereto, as a molecular marker, preferably as a molecular marker for an isolated polynucleotide according to SEQ ID No: 1, or a polynucleotide that has at least 50%, preferably at least 60%, more preferably at least 70%, even more preferably at least 90%, most preferably at least 95% sequence identity to the nucleotide sequence of SEQ ID NO: 1, or as a molecular marker for a polynucleotide according to any of the claims 7-10, preferably having alpha-farnesene synthase activity and/or beta-farnesene synthase activity.

Also provided is for the use of a polynucleotide according to SEQ ID No: 1, or a polynucleotide that has at least 50%, preferably at least 60%, more preferably at least 70%, even more preferably at least 90%, most preferably at least 95% sequence identity to the nucleotide sequence of SEQ ID NO: 1. for mapping a molecular (DNA) marker linked to the nucleotide sequence according to the invention.

As the skilled person is aware, a genetic (or molecular) marker is a gene or DNA sequence with a known location on a chromosome and associated with a particular gene or trait. It can be described as a variation, which may arise due to mutation or alteration in the genomic. loci, that can be observed. A genetic marker may be a short DNA sequence, such as a sequence surrounding a single base-pair change (single nucleotide polymorphism, SNP), or a long one, like minisatellites.

In the current invention, the marker can be (a fragment of) the polynucleotide according to SEQ ID No: 1, or a polynucleotide that has at least 50%, preferably at least 60%, more preferably at least 70%, even more preferably at least 90%, most preferably at least 95% sequence identity to the nucleotide sequence of SEQ ID NO: 1.

Mapping of genetic markers in or in the vicinity of a gene is a procedure which can be performed quite easily by the average molecular-biological skilled person and which is for instance described in Lefebvre, V. & A. M. Chevre. Tools for marking plant disease and pest resistance genes: a review. Agronomie 15, 1995 (1): 3-19; Michelmore, R. W. Molecular approaches to manipulation of disease resistance genes. Annual Review of Phytopathology 33 (1995): 393-427; Michelmore, R. W., R. V. Kesseli & E. J. Ryder. Genetic mapping in lettuce. In: R. L. Phillips & I. K. Vasil (eds.) DNA-based markers in plants, Kluwer Acad. Publishers, Dordrecht, 1994, pp. 223-239; Winter, P. & G. Kahl. Molecular marker technologies for plant improvement. World Journal of Microbiology & Biotechnology, 1995, 11 (4): 438-448.

The invention also relates to diagnostic kits, comprising oligonucleotides according to the invention, for the detection of the presence or absence of a farnesene synthase gene according to the invention within a genotype under study. Such a diagnostic kit circumvents the use of laborious assays to screen for genotypes forming for example alpha-farnesene and/or beta-farnesene or not.

Furthermore the invention relates to genetic constructs comprising a polynucleotide sequence according to the invention, preferably encoding a farnesene synthase according to the invention, e.g. a farnesene synthase having alpha-farnesene synthase activity and/or beta-farnesene activity. Such genetic construct preferably further comprise regulatory sequences functional in plant cells, said regulatory sequences, like promoters, being either homologous or heterologous to the coding sequences of the polynucleotides, for example a polynucleotide according to SEQ.ID.NO:1, according to the invention.

In another embodiment, the genetic construct comprises in the 5'-3'direction an open reading frame polynucleotide encoding a polypeptide according to the invention. In a further embodiment, the genetic construct comprises in the 5'-3'direction a polynucleotide that hybridizes to a polynucleotide encoding a polypeptide according to the invention, preferably under stringent conditions.

The invention relates also to a DNA vector comprising a DNA construct according to the invention. Suitable vectors can be cloning vectors, transformation vectors, expression vectors, and so on, and which are well known to those skilled in the art.

Furthermore, cells harbouring a vector comprising a genetic construct as described above, for example comprising a polynucleotide according to SEQ.ID.NO:1, or part thereof, or homologous thereto, are within the scope of the invention. Moreover, cells carrying a genetic construct according to the invention, are within the scope of this invention.

In one preferred embodiment of the invention, a genetically transformed plant is obtained by introducing a polynucleotide according to the invention within the genome of said plant, using standard transformation techniques. Preferably said genetically transformed plant functionally expresses the farnesene synthase according to the invention, e.g. a farnesene synthase having an amino acid sequence according to SEQ.ID.NO:2.

In another embodiment of the invention, the polynucleotides according to the invention can be transferred, using generally known transformation techniques, to heterologous systems, such as but not limited to melon, tobacco, *Arabidopsis thaliana*, potato, sugar beet, rapeseed, cucumber, pepper, eggplant, cotton, maize, squash, watermelon and lettuce. Also included are such systems like bacteria and yeasts. Introducing a polynucleotide according to the invention into such systems allows for the production of, for example, polypeptides according to the invention, and, either in vivo or in vitro utilisation of such peptides for the production of farnesene, preferably alpha-farnesenes and beta-farnesenes.

In another embodiment of the invention there is provided for the seeds derived from a transgenic plant or plant cell according to the invention, and for example comprising a polynucleotide according to the invention, for example according to SEQ.ID.NO1.

In another aspect there is provided for a method of preparing alpha-farnesene and/or beta-farnesene comprising the steps of culturing a cell which has been genetically modified with a polynucleotide according to the invention to provide increased alpha-farnesene synthase and/or beta-farnesene synthase activity; optionally, providing the cell with farnesyl diphosphate; and separating the alpha-farnesene and/or beta-farnesene produced. Also included is this method is culturing a cell derived from tomato, in particular the tomato used in the Examples.

In a further embodiment there is provided a method for modulating the alpha-farnesene and beta-farnesene production of a plant, the method comprising increasing or decreasing the expression of a farnesene synthase having a polypeptide sequence according to the invention, wherein said increasing or decreasing is achieved by genetic modification to alter the expression of a polynucleotide encoding for said polypeptide.

The polynucleotides and polypeptides, and fragments thereof, and preferably encoding for or having farnesene synthase activity, preferably alpha-farnesene activity and/or beta-farnesene activity, as described herein, have various applications of which some are described herein but which are not limiting the scope of the invention. For example, the polynucleotides according to the invention can be used for creating plant (over)expressing a farnesene synthase according to the invention, and which can confer improved control of aphid behaviour and towards repelling herbivorous insects, for example white flies.

The present invention will be further described in the examples in view of the isolation of a polynucleotide according to the invention. The following examples merely Illustrate the best mode now contemplated for practising the invention, but should not be construed to limit the invention.

EXAMPLES

Plant Material and Trichome, RNA and mRNA Isolation

A tomato plant (*Solanum lycopersicon* cultivar Money Maker) was grown in soil in a greenhouse with day/night temperatures of 23° C. to 18° C. and a 16/8 h light/dark regime for 4 weeks. Cuttings of stems with meristematic tissue from the same plant were made, which were placed in soil and grown again for another 3 weeks. Trichomes of the stem and petioles were collected at the bottom of a 50 ml tube by vortexing petiole and stem segments frozen in liquid nitrogen.

RNA of trichomes was isolated using Qiagen RNeasy plant Mini kit (Dusseldorf, Germany) according to the manufacturer's protocol for plant cells and tissue. Lysis was carried out using the supplied RLT buffer. Messenger RNA was isolated from the pool of total RNA using Promega's (Madison, Wis., USA) PolyAtract mRNA isolation system III according to the manufacturer's protocol. mRNA was isolated from total RNA with an efficiency of 0.71%.

mRNA Amplification and Double Strand cDNA Synthesis

MessageAmp II a RNA amplification kit from Ambion (Austin, Tex., USA) was used to amplify trichome mRNA. 100 ng of mRNA was used as input for amplification. Amplification was carried out according to the manufacturer's protocol. The yield of amplified RNA was 171 µg and the size distribution was as expected, ranging from ~400 to 3,000 bases.

Random hexamer primers (ordered from MWG Operon, Ebersberg, Germany) were used to synthesize first strand cDNA from this amplified RNA in batches using 10 µg of RNA in 20 µl reactions. Random primers at a final concentration of 62.5 nM were combined with amplified RNA and incubated at 70° C. for 5 minutes after which it was stored on ice. RevertAid M-MuIV reverse transcriptase (200 units) from Fermentas Life Sciences (St. Leon-Rot, Germany) in combination with supplied buffer was added. Nucleotides were added to a final concentration of 1 mM. cDNA synthesis was carried out 42° C. for 90 minutes. Directly thereafter, tubes were transferred to ice and second-strand synthesis was performed using Fermentas RNase H and DNA polymerase I from *E. coli*. To each 20-µl reaction tube 8 µl of the supplied DNA polymerase I reaction buffer was added along with 1 unit RNase H and 30 units DNA polymerase I. Reaction volume was increased with water to 100 µl. All components were added cold and the second strand synthesis reaction was carried out at 15° C. for 2 hours.

Massive Parallel Pyro-sequencing and Data Analysis

Shearing of ds-cDNA, library preparation, 454-sequencing and contig alignments were performed in accordance with methods described in the art and known to the skilled person. Processing involved a bar-coded 454-sequencing adapter, with each of the 5 mutants carrying a distinct bar-code (see for example WO2007073165, WO2007037678 or WO2007073165, wherein the distinct bar-code is described as a tag or identifier). Pyrosequencing itself is known in the art. The technology is further applied in e.g. WO 03/004690, WO 03/054142, WO 2004/069849, WO 2004/070005, WO 2004/070007, and WO 2005/003375 (all in the name of 454 Life Sciences), which are herein incorporated by reference. Methods of alignment of sequences for comparison purposes are well known in the art. Various programs and alignment algorithms are described in: Smith and Waterman (1981) Adv. Appl. Math. 2:482; Needleman and Wunsch (1970) J. Mol. Biol. 48:443; Pearson and Lipman (1988) Proc. Natl. Acad. Sci. USA 85:2444; Higgins and Sharp (1988) Gene 73:237-244; Higgins and Sharp (1989) CABIOS 5:151-153; Corpet et al. (1988) Nucl. Acids Res. 16:10881-90; Huang et al. (1992) Computer Appl. in the Biosci. 8:155-65; and Pearson et al. (1994) Meth. Mol. Biol. 24:307-31, which are herein incorporated by reference. Altschul et al. (1994) Nature Genet. 6:119-29 (herein incorporated by reference) present a detailed consideration of sequence alignment methods and homology calculations.

Identification and Cloning of Tomato Sesquiterpene Synthase SlSST3

One of the contigs generated from the 454-sequence reads (lcl-CL117Contig1) with a length of 793 by had amongst the contigs, a higher degree of identity to a Fabiana imbricata sesquiterpene synthase (without known function) mRNA (AY860847). To obtain a full-length clone of this tomato cDNA, PCR amplification was performed on a cDNA library constructed with mRNA from tomato trichomes. HybriZAP-2.1 XR library construction kit and HybriZAP-2.1 XR cDNA synthesis kit from Stratagene (Cedar Creek, Tex., USA) were used according to the manufacturer's protocol. The size of the primary cDNA library was 2.5×106 Plaque Forming Units (PFU)/µg phage arm. The primary library was amplified according to the manufacturer's protocol. This amplified cDNA library was excised using the Mass Excision Protocol described by the manufacturer. This excised library was used to PCR amplify 3' and 5' parts of the cDNA fragment using primers 1-6 (see primer list in Table 1 below).

TABLE 1

Primer list

| 1 | GGTATTATGGAAAGAAAGTACCAAC | 6F3_E |
| 2 | TTCCATAAATGAGATGAAAAAGGTC | 6F4_E |
| 3 | TTCCTTGAAATTTCCTTGGTCATT | 6R4_E |
| 4 | CTCAACATTCCTTCTACATCC | 6R5_E |
| 5 | TAATACCACTACAATGGATC | pActF |
| 6 | AATACGACTCACTATAGGGCTCTA | T7long |
| 7 | CACCATGGAGTTGTGCACACAAAC | E6TopoF |
| 8 | CTATATAATAGGATCAACTAGTATATCAGAGATG | E6TopoR |
| 9 | TTCTTTTTCTTGTTGTCATCGG | E6flR2 |
| 10 | CTTGTGAAAAATGGAGTTGTGC | E6flF |

For the 5' part of this cDNA a PCR was performed with primer 6R5E and pActF (see primer list) and for the 3' part of this cDNA primers 6F4E and T7long was used. The excised cDNA library was used as template with 0.25 units of Phusion Hot Start polymerase from Finnzymes (Espoo, Finland) along with supplied buffer, each primer in a concentration of 0.4 mM and dNTPs in a concentration of 0.2 mM in a reaction volume of 25 µl. MgCl2 was added to the PCR mix in an end concentration of 0.3 mM. The T1 thermocycler from Biometra (Gottingen, Germany) was used with the following program:

Step 1. 98° C. for 1 minute
Step 2. 98° C. for 10 seconds
Step 3. 56° C. for 30 seconds
Step 4. 72° C. for 45 seconds
Step 5. Go to step 2; repeat 34 times
Step 6. 72° C. for 5 minutes
Step 7. 4° C. until taken from thermocycler.

The reaction products were diluted 20 times with water to use as template for re-amplification. Re-amplification of the 5' part was carried out using primers 6R4E and pActF and for re-amplification of the 3' part primers 6F3E and T7long were used. PCR conditions were the same as for the primary PCRs.

PCR products of the re-amplification reactions were cut from gel and isolated using Gel Extraction Kit from QIAGEN according to the manufacturer's protocol. PCR products were sequenced using ABI Prism BigDye Terminator v1.1 Cycle Sequencing Kit.

Together with the newly sequenced cDNA fragments, the contig obtained from the 454-sequences could be expanded to full coding sequence by assembling overlapping sequence fragments. New primers were designed (primer E6flR2 and E6flF, see primer list) which were used to PCR amplify full coding sequence from the excised cDNA library. Full-length amplification was performed with Phusion Hot Start polymerase from Finnzymes as described above.

The PCR fragment obtained in this PCR reaction was excised from gel and isolated using Gel Extraction Kit from QIAGEN according to the manufacturer's protocol. Subsequently, this purified fragment was cloned into pCR2.1 cloning vector using the TA cloning kit from Invitrogen (Carlsbad, Calif., USA) according to the manufacturer's protocol. Plasmid was transferred to One Shot TOP10 chemically competent E.coli cells (supplied with the kit). A liquid culture was started from which plasmid was isolated using GeneJET Plasmid Miniprep Kit from Fermentas, according to the manufacturer's protocol and plasmid insert was sequenced.

Full length coding sequence was amplified from the plasmid with primer E6TopoF and E6TopoR using Phusion Taq Polymerase as described above. The PCR fragment was isolated from gel as described above. This full-length cDNA was cloned into pET TOPO vector using the Champion pET200 Directional TOPO Expression Kit from Invitrogen as described in the manufacturer's protocol.

Subsequently the plasmid was transferred to One Shot Top10 Chemically competent E. coli cell, supplied with the kit. Plasmids were isolated and sequenced. The sequence was identical to the first full-length cDNA as sequenced from the pCR2.1 cloning vector. The coding sequence of SlSST3 is shown in SEQ. ID. No:1. SEQ. ID. No:2 shows the deduced amino acid sequence.

Expression of SlSST3 Protein in E. Coli

The pET200 plasmid containing SlSST3 was transformed to BL21 Star (DE3) One Shot Chemically competent E. coli cells. Liquid cultures were grown overnight at 37° C. The following day a 50 ml culture was inoculated with 2.5 ml of the overnight culture and grown to optical density at 600 nm of 0.5. The culture was transferred to room temperature and induced with isopropyl beta-D-1-thiogalactopyranoside (IPTG) from Roche (Basel, Switzerland) at a final concentration of 1 mM. As a negative control a culture with a dummy insert in the pET200 vector (an R2R3-type MYB transcription factor (Genebank accession number AY705977) with no terpene synthase activity) was used. Uninduced controls of both cultures were taken along. After 3 hours of induction, two aliquots of 1 ml were taken from each culture after which the remainder of the cells was collected by centrifugation at 4° C. at 2,000 g for 15 minutes and subsequent aspiration of the medium. Cell pellets were frozen in liquid nitrogen and stored at −80° C. until enzyme assays were performed.

Figure 1:
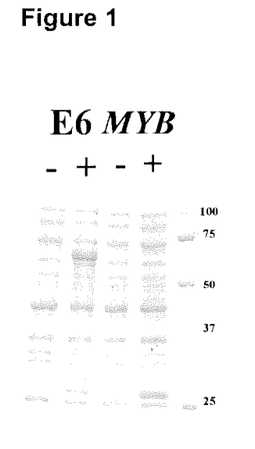
FIG. 1 shows a scan of a stained gel. An acryl amide gel of total proteins from induced (+) and uninduced (−) cells with plasmid containing SISST3 and MYB transcription factor was stained with Coomassie Brilliant Blue (0.25% CBB (w/v), 30% methanol (v/v) and 10% acetic acid).

Optical density of the 1 ml aliquots was determined at 600 nm. Cells were collected by centrifugation at 2.000 g at 4° C. for 10 minutes and aspiration of the medium. Cells of one of the induced and one of the uninduced aliquot were resuspended in 50 μl per OD unit terpene synthase buffer (as described by Van Schie et al. Plant Mol Biol. 2007 June; 64(3):251-63). After disruption of the cells by incubation with 1 μg lysozyme on ice for 30 minutes and sonification, soluble protein fraction was collected by centrifugation at 12,000 g for 30 minutes at 4° C. The other induced and uninduced cell pellets were resuspended in 50 μl per OD unit PBST (0.8% NaCl (w/v), 0.02% KCl (w/v), 0.144% Na2HPO4 (w/v), 0.02% KH2PO4 (w/v) and 0.02% (v/v) Tween-20). To both total and soluble protein fractions, one-third volume 4× Sample buffer (8% SDS (w/v), 40% glycerol (w/v), 20% beta-mercaptoethanol (v/v) 240 mM Tris-HCl pH 6.8 and 0.08% brome-phenol blue (w/v)) was added and samples were placed in boiling water for 5 minutes. A 15 μl protein sample was electrophoresed on a 10% acryl amide gel. An acryl amide gel of total proteins from induced and uninduced cells with plasmid containing SISST3 and MYB transcription factor was stained with Coomassie Brilliant Blue (0.25% CBB (w/v), 30% methanol (v/v) and 10% acetic acid). A scan of this stained gel is shown in FIG. 1.

Figure 2:
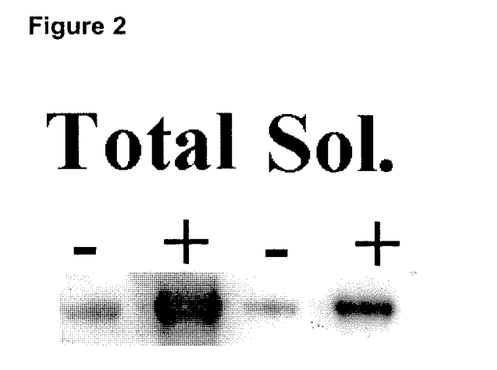
FIG. 2 shows a picture of chemoluminescence of a nitrocellulose blot. Total and soluble protein fractions of induced (+) and uninduced (−) cells with plasmid containing SISST3 were run on a 10% acryl amide gel. After electrophoresis of the samples, proteins were blotted on nitrocellulose. The blot was blocked with a 5% powdery milk solution in PBST for an hour. Overnight the blot was incubated in 10 ml PBST with 5% powdery milk with penta-His antibody (catalogue nr. 34660, batch nr. 130167450) from QIAGEN. The blot was washed 3 times with PBST and subsequently incubated for one hour in PBST with 5% (w/v) powdery milk and horseradish peroxidase-coupled goat anti-mouse IGG antibody from Pierce, Rockford, Ill., USA after which it was washed 3 times in PBST. Peroxidase activity was detected by enhanced chemoluminescence (Amersham, Buckinghamshire, UK).

Total and soluble protein fractions of induced and uninduced cells with plasmid containing SISST3 were run on a 10% acryl amide gel. After electrophoresis of the samples, proteins were blotted on nitrocellulose. The blot was blocked with a 5% powdery milk solution in PBST for an hour. Overnight the blot was incubated in 10 ml PBST with 5% powdery milk with penta His antibody (catalogue nr. 34660, batch nr. 130167450) from QIAGEN. The blot was washed 3 times with PBST and subsequently incubated for one hour in PBST with 5% (w/v) powdery milk and horseradish peroxidase-coupled goat anti-mouse IGG antibody from Pierce, Rockford, Ill., USA after which it was washed 3 times in PBST. Peroxidase activity was detected by enhanced chemoluminecence (Amersham, Buckinghamshire, UK). A picture of the chemoluminescence can be seen in FIG. 2.

Functional Analysis of SISST3 Protein

Cell pellets of the rest of the cultures were assayed for sesquiterpene synthase activity. Sesquiterpene synthase assays were performed as described by Van Schie et al. Plant Mol Biol. 2007 June; 64(3):251-63, and incorporated herewith by reference.

Analysis of the reaction products was carried out with Ni-purified protein on a GC-MS TOF with a DB-5 column as described by Van Schie et al. Plant Mol Biol. 2007 June; 64(3):251-63, or as described by Ament et al (2004) Plant Physiol. 135:2025-2037, hereby incorporated by reference.

Figure 3:
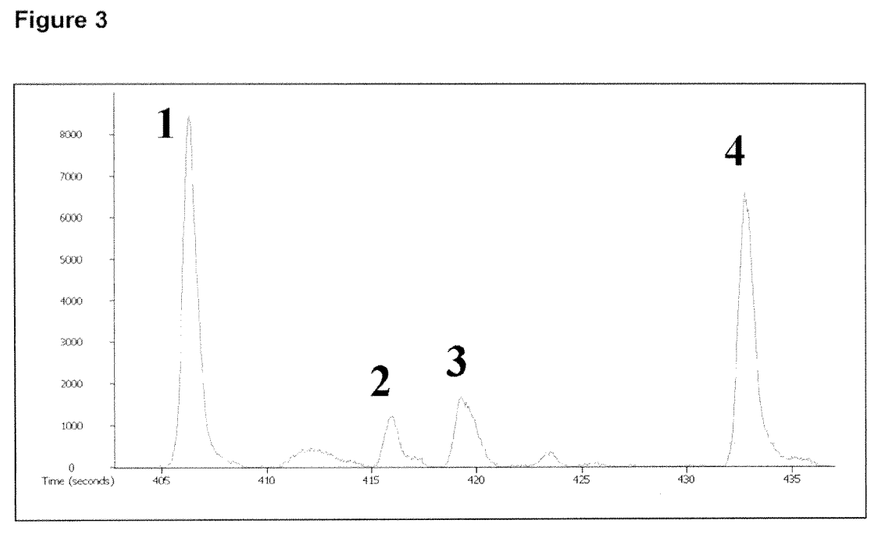
FIG. 3 shows GC-MS spectra of ion 69 for Ni-purified SISST3 and Myb transcription factor protein assayed with FPP zoomed in on retention time 402 seconds till 436 seconds. Products of peak 1, 2, 3 and 4 were identified as (E) beta-farnesene (peak 1), (Z,E) alpha-farnesene (peak 2), (E,E) alpha-famesene and (Z,Z) alpha-farnesene (both in peak 3) and (E)-nerolidol (peak 4), using authentic standards and comparison of ion spectra and retention times.

FIG. 3 shows GC-MS spectra of ion 69 for Ni-purified SISST3 and Myb transcription factor protein assayed with FPP zoomed in on retention time 402 seconds till 436 seconds. Products of peak 1, 2, 3 and 4 were identified as (E) beta-farnesene (peak 1), (Z,E) alpha-farnesene (peak 2), (E,E) alpha-farnesene and (Z,Z) alpha-farnesene (both in peak 3) and (E)-nerolidol (peak 4), using authentic standards and comparison of ion spectra and retention times.

Figure 5:
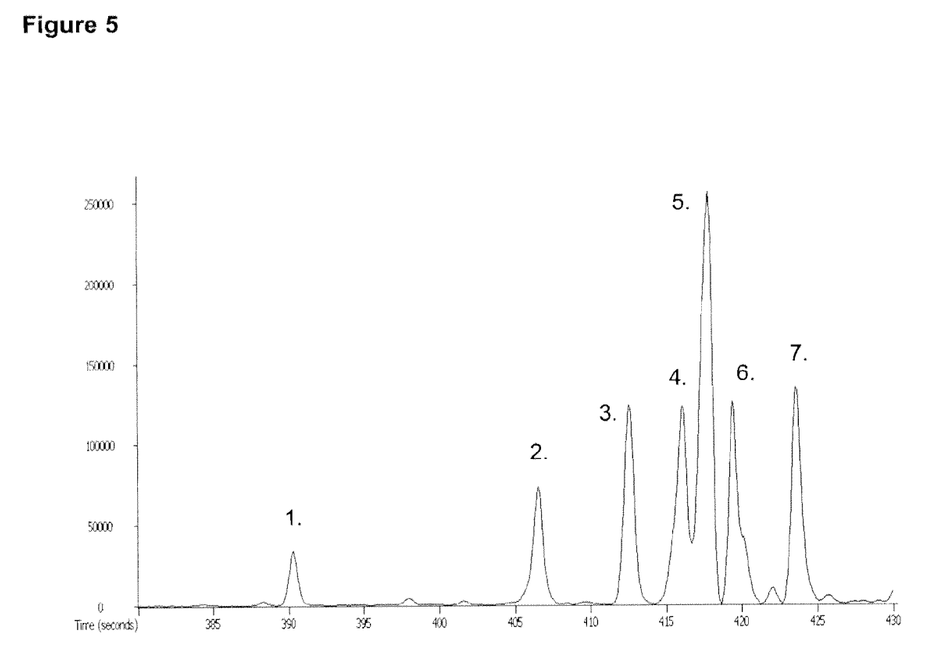
FIG. 5 shows a further GC-MS chromatogram of protein extracts from E.coli cells expressing tomato farnesene synthase assayed with FPP. Peak 1. beta-elemene (*). 2. (E) beta-farnesene. 3. unknown sesquiterpene (*). 4. (Z,E) alpha-farnesene. 5. (+)-valencene (*). 6. (E,E) alpha-farnesene. 7. unknown sesquiterpene (*). (*). Peaks indicated with (*) are identified on basis of mass spectra, all others based on mass spectra and comparison of retention time of pure standards.

FIG. 5 shows a further GC-MC chromatogram of protein extracts from E.coli cells expressing tomato farnesene synthase assayed with FPP. Peak 1. beta-elemene (*). 2. (E) beta-farnesene. 3. unknown sesquiterpene (*). 4. (Z,E) alpha-farnesene. 5. (+)-valencene (*). 6. (E,E) alpha-farnesene. 7. unknown sesquiterpene (*). (*). Peaks indicated with (*) are identified on basis of mass spectra, all others based on mass spectra and comparison of retention time of pure standards.

Figure 4:
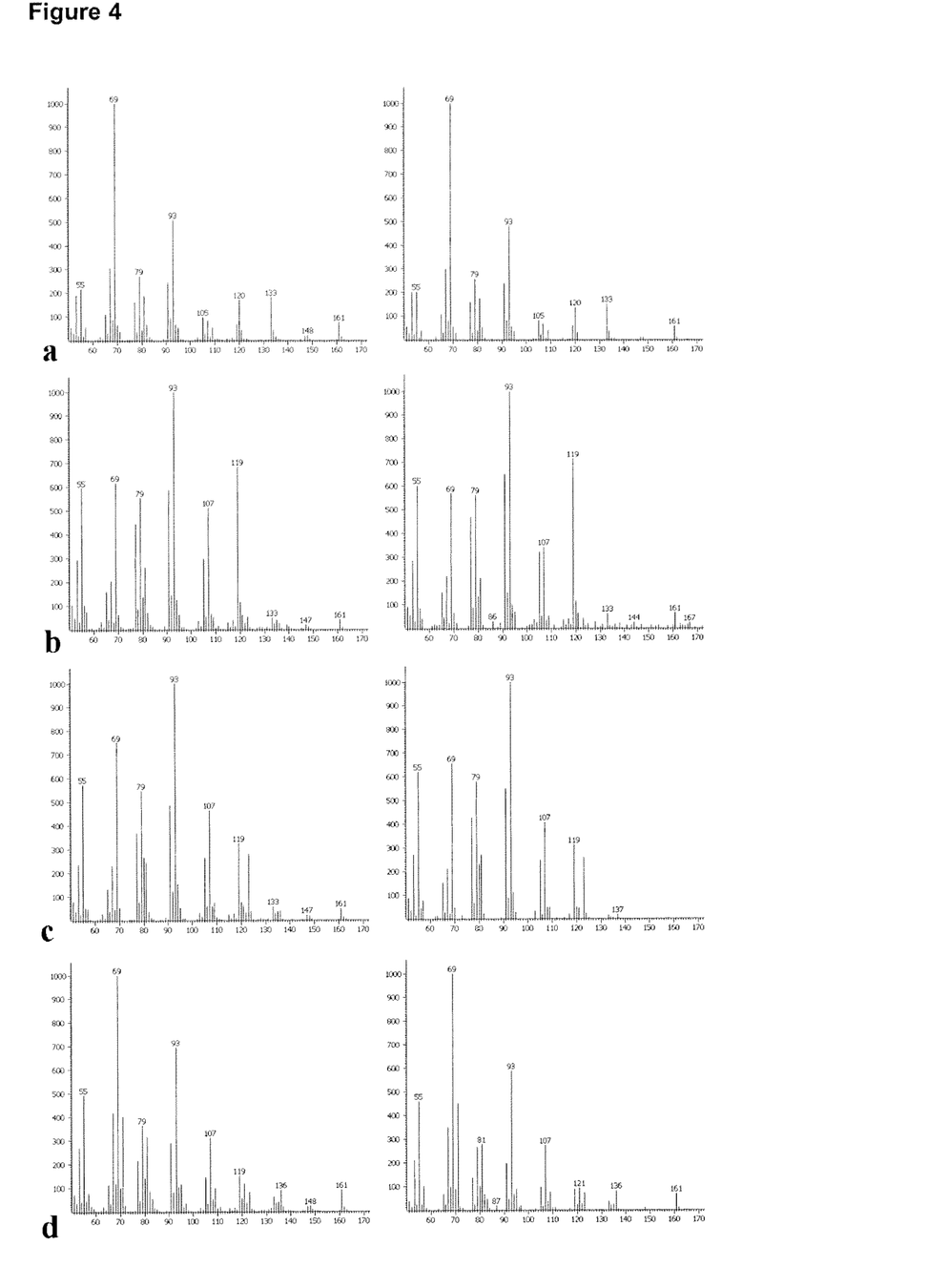

Pure (E) beta-farnesene was kindly provided by Prof. Dr. W. Boland. Mass spectra of this sesquiterpene and mass spectrum peak 1 are shown in FIG. 4a. A mixture of (Z,E) alpha-farnesene and (E,E) alpha-farnesene was obtained from Sigma. Mass spectra of (Z,E) alpha-farnesene and peak 2 are shown in FIG. 4b and FIG. 4c shows the mass spectra of (E,E) alpha-farnesene and peak 3. (E) Nerolidol was obtained from Sigma. Mass spectra of this sesquiterpene and of peak 4 are shown in FIG. 4d.

These results show that SISST3, cloned from tomato trichome cDNA encodes a farnesene synthase, having (predominantly) beta-farnesene synthase activity and in addition alpha-farnesene activity.

Figure 6:
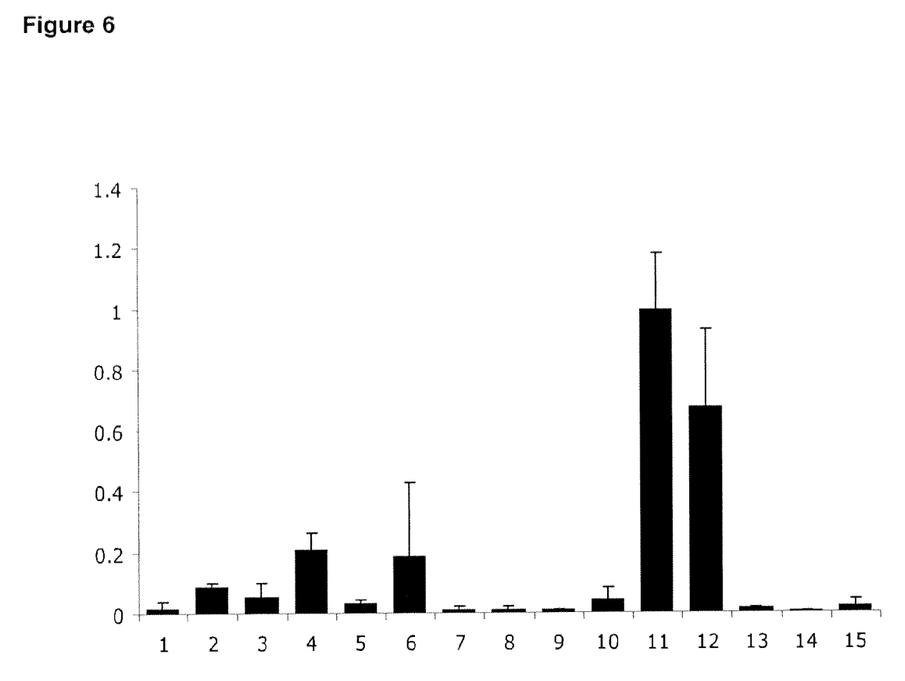
In FIG. 6, the spatial expression of the farnesene synthase (according to the invention) in Solanum lycopersicum as determined by quantitative RT-PCR and corrected for the constitutive RCE1 expression on cDNA from different tissues of Solanum lycopersicum is shown. Bar graphs represent the average of two independent predicates. Maximum is indicated by error bars. cDNA is synthesized from RNA isolated from 1. Roots; 2. Flower buds; 3. Stamens; 4. Petals; 5. Sepals; 6. Immature green fruits; 7. Breaker fruits; 8. Turning fruits; 9. Red fruits; 10. Petioles; 11.Stems; 12. Plant tops; 13. Young leaves; 14. Mature leaves; 15. Senescent leaves.

Relative Expression Levels of Tomato Farnesene Synthase in Various Tissues and Organs In FIG. 6, the spatial expression of the farnesene synthase (according to the invention) in *Solanum lycopersicum* as determined by quantitative RT-PCR and corrected for the constitutive RCE1 expression on cDNA from different tissues of *Solanum lycopersicum* is shown. Bar graphs represent the average of two independent predicates. Maximum is indicated by error bars. cDNA is synthesized from RNA isolated from 1. Roots 2. Flower buds 3. Stamens 4. Petals 5. Sepals 6. Immature green fruits 7. Breaker fruits 8. Turning fruits 9. Red fruits 10. Petioles 11. Stems 12. Plant tops 13. Young leaves 14. Mature leaves 15. Senescent leaves.

BRIEF DESCRIPTION OF THE DRAWINGS

FIG. 4a shows mass spectra of the sesquiterpene pure (E) beta farnesene and mass spectrum peak 1 of FIG. 3. A mixture of (Z,E) alpha-farnesene and (E,E) alpha-farnesene was obtained from Sigma. Mass spectra of (Z,E) alpha-farnesene and peak 2 of FIG. 3 are shown in FIG. 4b, and FIG. 4c shows the mass spectra of (E,E) alpha-farnesene and peak 3 of FIG.

3. (E)-nerolidol was obtained from Sigma. Mass spectra of this sesquiterpene and of peak 4 of FIG. 3 are shown in FIG. 4d.

The invention claimed is:

1. An isolated cDNA sequence according to SEQ ID No: 1, or a polynucleotide that has at least 90% identity to the cDNA sequence of SEQ ID NO: 1, wherein said polynucleotide encodes a polypeptide with alpha-farnesene synthase activity and beta-farnesene synthase activity.

2. An isolated polypeptide according to SEQ ID NO: 2, or a polypeptide that has at least 90% sequence identity to the amino acid sequence according to SEQ ID NO: 2, wherein said polypeptide has alpha-farnesene synthase activity and beta-farnesene synthase activity.

3. A genetic construct comprising a cDNA sequence of claim 1.

4. A genetic construct comprising in the 5'-3' direction a cDNA encoding a polypeptide of claim 2.

5. A genetic construct comprising in the 5'-3' direction a polynucleotide which hybridizes under high stringent conditions to a polynucleotide encoding a polypeptide of claim 2, wherein said high stringent conditions comprise about 65° C. in a solution comprising about 1 M salt, and washing at 65° C. in a solution comprising about 0.1 M salt.

6. A vector comprising a genetic construct according to any one of claims 3-5.

7. A host cell comprising a genetic construct of any one of claims 3-5.

8. A transgenic plant or plant cell comprising a genetic construct of any one of claims 3-5.

9. Seeds derived from a transgenic plant or plant cell according to claim 8, comprising a genetic construct of any one of claims 3-5.

10. A method of preparing alpha-farnesene and/or beta-farnesene comprising the steps of culturing a cell which has been genetically modified with a polynucleotide of claim 1 to provide increased alpha-farnesene synthase and/or beta-farnesene synthase activity; and optionally, providing the cell with farnesyl diphosphate; and separating the alpha-farnesene or beta-farnesene produced.

11. A method for modulating the alpha-farnesene and beta-farnesene production of a plant, the method comprising increasing the expression of an alpha-farnesene synthase and beta-farnesene synthase having a polypeptide sequence as defined in claim 2, wherein said increasing is achieved by genetic modification to alter the expression of a polynucleotide encoding said polypeptide.

* * * * *

UNITED STATES PATENT AND TRADEMARK OFFICE
CERTIFICATE OF CORRECTION

| | |
|---|---|
| PATENT NO. | : 8,674,175 B2 |
| APPLICATION NO. | : 13/132702 |
| DATED | : March 18, 2014 |
| INVENTOR(S) | : Ferrara et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 273 days.

Signed and Sealed this
Ninth Day of August, 2016

Michelle K. Lee
*Director of the United States Patent and Trademark Office*

SEQUENCE LISTING

<160> NUMBER OF SEQ ID NOS: 2

<210> SEQ ID NO 1
<211> LENGTH: 1665
<212> TYPE: DNA
<213> ORGANISM: Solanum lycopersicon

<400> SEQUENCE: 1

```
atggagttgt gcacacaaac cgttgcagcg gatcatgaag ttataattac acgtcgctct    60
ggtagtcatc atcctacttt atggggtgac cattttcttg cctatgctga tcttcgggga   120
gccaatgaag gggaagagaa gcaaaatgaa gacctaaaag aagaagtgag aaagatgcta   180
gtgatggctc cttcaaagtc tttggaaaaa cttgaactca tcaacacaat ccaatgtctt   240
ggtttaggtt atcattttca aagtgagatt gatgaatcat tgagttacat gtacactcat   300
tatgaagaat attcgattgg tgatcttcat gctattgctc tatgctttcg attacttagg   360
caacaaggtt attatgtctc atgtgatgca tttaagaagt tcactaatga ccaaggaaat   420
ttcaaggaag aattggttaa ggatgtagaa ggaatgttga gcttatatga ggcagcacaa   480
ttcagagtac atggagaaca aattcttgat gaagcactaa atttcaccat tgctcaattg   540
aaacaaattt tgcctaaatt gagcaactcc caacttgcac aacaaatcac aaatgcactc   600
aagtatccaa ttaaagatgg cattgtgagg gtagaaacaa gaaaatacat atcattttac   660
caacaaaatc aaaatcacaa tgaagtctta ctaaactttg ccaaattaga cttcaacatc   720
ttgcaaacat tgcataaaaa ggagctatct gatatgacaa ggtggtggaa aaagatggaa   780
ctagtgaaca cattaccttta tgcaagagac agattggtag agtgttactt ttggtgttta   840
ggcacctatt ttgagcctca gtatagcgtc gcaaggaaaa tgttgacaaa aatttcattc   900
tatatttcaa ttattgatga cacatatgat atttatggga aactagatga acttactcta   960
ttcactcagg caattgaaag gtggaatatt gatgcttcag aacagttacc attatatatg  1020
aagattattt accgtgatct tttagatgtt tatgatgaaa ttgagaaaga gttggcaaat  1080
gaaaacaagt cattttttagt caattattcc ataaatgaga tgaaaaaggt cgtaagggggt  1140 tactttcaag aggcaaaatg gtattatgga aagaaagtac caacaatgga gcaatatatg  1200
aagaatggaa tttcaacaag tgcttacata ttgctaacaa ctacttcttg gttagcaatg  1260
ggaaatgtag caactaaaga tgcatttgat tgggtagcaa ctgaaccacc aatagttgtt  1320
gcttcttgtt acattataag attactcaat gatcttgtat cacatgagga agaacaaaaa  1380
cgaggaaatg cggcttctgc tgttgaatgt tatatgaatg aatatagcgt tacaaaggaa  1440
gaagcacaca taaaaataag agatataata gaaaattatt ggaaggattt gaatgaagaa  1500
tactttaaag tagatatgat tattatacca agagtttttgc tcatgtgtat aattaatctt  1560
acaagagtgg ctgagttcat atataaagat gaagatgctt atactttctc caaaaataac  1620
```

```
ttgaaagatg tcatctctga tatactagtt gatcctatta tatag           1665
```

<210> SEQ ID NO 2
<211> LENGTH: 554
<212> TYPE: PRT
<213> ORGANISM: Solanum lycopersicon

<400> SEQUENCE: 2

```
Met Glu Leu Cys Thr Gln Thr Val Ala Ala Asp His Glu Val Ile Ile
1               5                   10                  15

Thr Arg Arg Ser Gly Ser His His Pro Thr Leu Trp Gly Asp His Phe
                20                  25                  30

Leu Ala Tyr Ala Asp Leu Arg Gly Ala Asn Glu Gly Glu Glu Lys Gln
            35                  40                  45

Asn Glu Asp Leu Lys Glu Glu Val Arg Lys Met Leu Val Met Ala Pro
    50                  55                  60

Ser Lys Ser Leu Glu Lys Leu Glu Leu Ile Asn Thr Ile Gln Cys Leu
65                  70                  75                  80

Gly Leu Gly Tyr His Phe Gln Ser Glu Ile Asp Glu Ser Leu Ser Tyr
                85                  90                  95

Met Tyr Thr His Tyr Glu Glu Tyr Ser Ile Gly Asp Leu His Ala Ile
            100                 105                 110

Ala Leu Cys Phe Arg Leu Leu Arg Gln Gln Gly Tyr Tyr Val Ser Cys
        115                 120                 125

Asp Ala Phe Lys Lys Phe Thr Asn Asp Gln Gly Asn Phe Lys Glu Glu
    130                 135                 140

Leu Val Lys Asp Val Glu Gly Met Leu Ser Leu Tyr Glu Ala Ala Gln
145                 150                 155                 160

Phe Arg Val His Gly Glu Gln Ile Leu Asp Glu Ala Leu Asn Phe Thr
                165                 170                 175

Ile Ala Gln Leu Lys Gln Ile Leu Pro Lys Leu Ser Asn Ser Gln Leu
            180                 185                 190

Ala Gln Gln Ile Thr Asn Ala Leu Lys Tyr Pro Ile Lys Asp Gly Ile
        195                 200                 205

Val Arg Val Glu Thr Arg Lys Tyr Ile Ser Phe Tyr Gln Gln Asn Gln
    210                 215                 220

Asn His Asn Glu Val Leu Leu Asn Phe Ala Lys Leu Asp Phe Asn Ile
225                 230                 235                 240

Leu Gln Thr Leu His Lys Lys Glu Leu Ser Asp Met Thr Arg Trp Trp
                245                 250                 255

Lys Lys Met Glu Leu Val Asn Thr Leu Pro Tyr Ala Arg Asp Arg Leu
            260                 265                 270

Val Glu Cys Tyr Phe Trp Cys Leu Gly Thr Tyr Phe Glu Pro Gln Tyr
        275                 280                 285

Ser Val Ala Arg Lys Met Leu Thr Lys Ile Ser Phe Tyr Ile Ser Ile
    290                 295                 300

Ile Asp Asp Thr Tyr Asp Ile Tyr Gly Lys Leu Asp Glu Leu Thr Leu
305                 310                 315                 320

Phe Thr Gln Ala Ile Glu Arg Trp Asn Ile Asp Ala Ser Glu Gln Leu
                325                 330                 335

Pro Leu Tyr Met Lys Ile Ile Tyr Arg Asp Leu Leu Asp Val Tyr Asp
            340                 345                 350

Glu Ile Glu Lys Glu Leu Ala Asn Glu Asn Lys Ser Phe Leu Val Asn
        355                 360                 365
```

```
Tyr Ser Ile Asn Glu Met Lys Lys Val Val Arg Gly Tyr Phe Gln Glu
        370                 375                 380

Ala Lys Trp Tyr Tyr Gly Lys Lys Val Pro Thr Met Glu Gln Tyr Met
385                 390                 395                 400

Lys Asn Gly Ile Ser Thr Ser Ala Tyr Ile Leu Leu Thr Thr Thr Ser
                405                 410                 415

Trp Leu Ala Met Gly Asn Val Ala Thr Lys Asp Ala Phe Asp Trp Val
            420                 425                 430

Ala Thr Glu Pro Pro Ile Val Val Ala Ser Cys Tyr Ile Ile Arg Leu
        435                 440                 445

Leu Asn Asp Leu Val Ser His Glu Glu Glu Gln Lys Arg Gly Asn Ala
    450                 455                 460

Ala Ser Ala Val Glu Cys Tyr Met Asn Glu Tyr Ser Val Thr Lys Glu
465                 470                 475                 480

Glu Ala His Ile Lys Ile Arg Asp Ile Ile Glu Asn Tyr Trp Lys Asp
            485                 490                 495

Leu Asn Glu Glu Tyr Phe Lys Val Asp Met Ile Ile Ile Pro Arg Val
        500                 505                 510

Leu Leu Met Cys Ile Ile Asn Leu Thr Arg Val Ala Glu Phe Ile Tyr
            515                 520                 525

Lys Asp Glu Asp Ala Tyr Thr Phe Ser Lys Asn Asn Leu Lys Asp Val
        530                 535                 540

Ile Ser Asp Ile Leu Val Asp Pro Ile Ile
545             550
```